(12) United States Patent
Charles et al.

(10) Patent No.: US 7,168,954 B2
(45) Date of Patent: Jan. 30, 2007

(54) METHOD AND SYSTEM FOR PERIODONTAL CHARTING

(75) Inventors: Christine A. Charles, Teaneck, NJ (US); Mei-Miau Wu, Morris Plains, NJ (US); John F. Coelho, Morristown, NJ (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 525 days.

(21) Appl. No.: 10/719,278

(22) Filed: Nov. 21, 2003

(65) Prior Publication Data

US 2005/0112527 A1    May 26, 2005

(51) Int. Cl.
G09B 23/28    (2006.01)

(52) U.S. Cl. .................... 434/263; 434/430

(58) Field of Classification Search .......... 434/219, 434/262, 263, 365, 366, 369, 430; 433/24, 433/26, 29, 68, 229

See application file for complete search history.

(56) References Cited

U.S. PATENT DOCUMENTS

| | | | | | |
|---|---|---|---|---|---|
| 1,338,068 | A | * | 4/1920 | Bush | 433/26 |
| 1,449,318 | A | * | 3/1923 | Fish | 33/1 A |
| 1,458,782 | A | * | 6/1923 | Shapiro | 433/26 |
| 1,654,387 | A | * | 12/1927 | Stenz | 434/263 |
| 5,244,394 | A | * | 9/1993 | Serabian-Musto | 434/263 |
| 5,743,730 | A | * | 4/1998 | Clester et al. | 433/26 |

OTHER PUBLICATIONS

"All Pets Dental: The Dental Chart", Oct. 31, 2000 [retrieved online Jun. 22, 2006].*
"Family Gentle Dental Care", Jul. 25, 2001 [retrieved online Jun. 22, 2006].*
"Perio Dental Chart", May 25, 2003 [retrieved online Jun. 22, 2006].*
"Innobate Dental Chart View", 2002 [retrieved online Jun. 22, 2006].*
Transcript for Howard Proskin, Sitewise Score Transitions and Odds Ratios as Supplemental Assessments of Treatment Effects in Gingivitis Studies, Scientific Program, Nov. 14, 2000.

* cited by examiner

*Primary Examiner*—Kurt Fernstrom
(74) *Attorney, Agent, or Firm*—Karen G. Horowitz; Evan J. Federman

(57) ABSTRACT

Methods and systems for graphically depicting gum tissue and teeth for illustrating gingival health and plaque reduction. The relative risk as one type of statistical methods for comparing two treatments of different therapeutic agents for gingivitis and plaque are displayed. The upper and lower sets of teeth are represented in rows or groups of teeth separated by rows of boxes which depict the result of various treatments by various therapeutic agents.

31 Claims, 6 Drawing Sheets

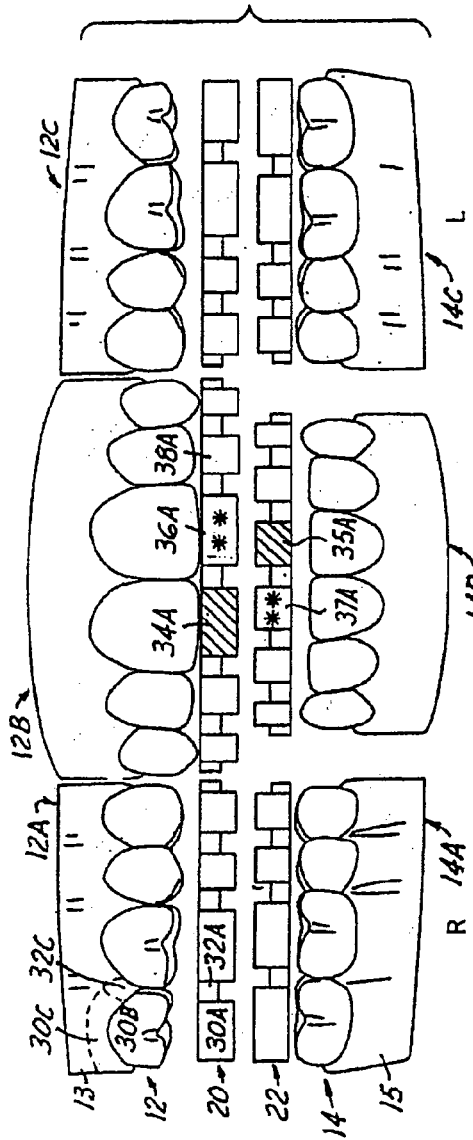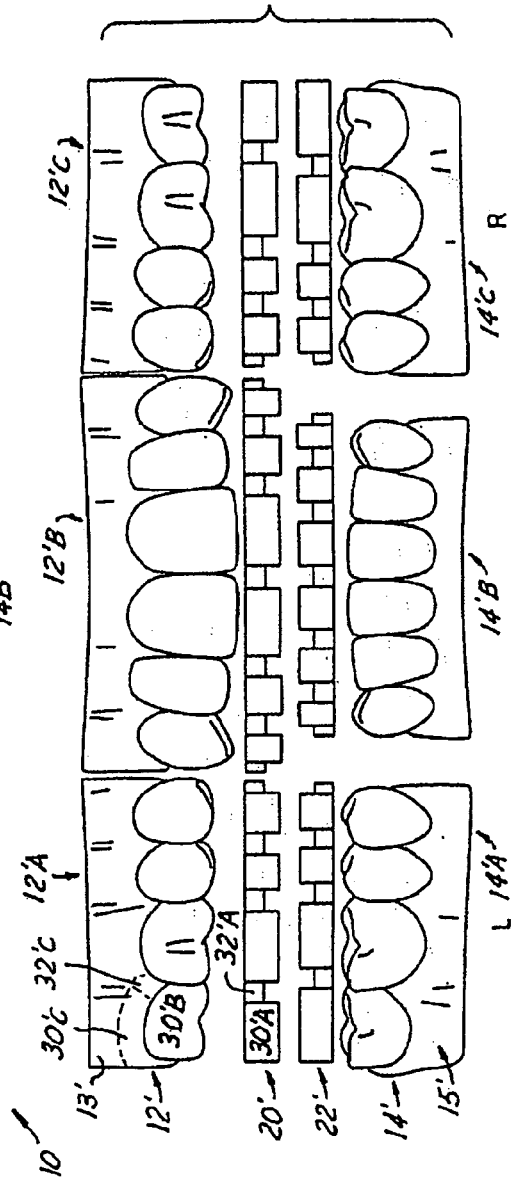

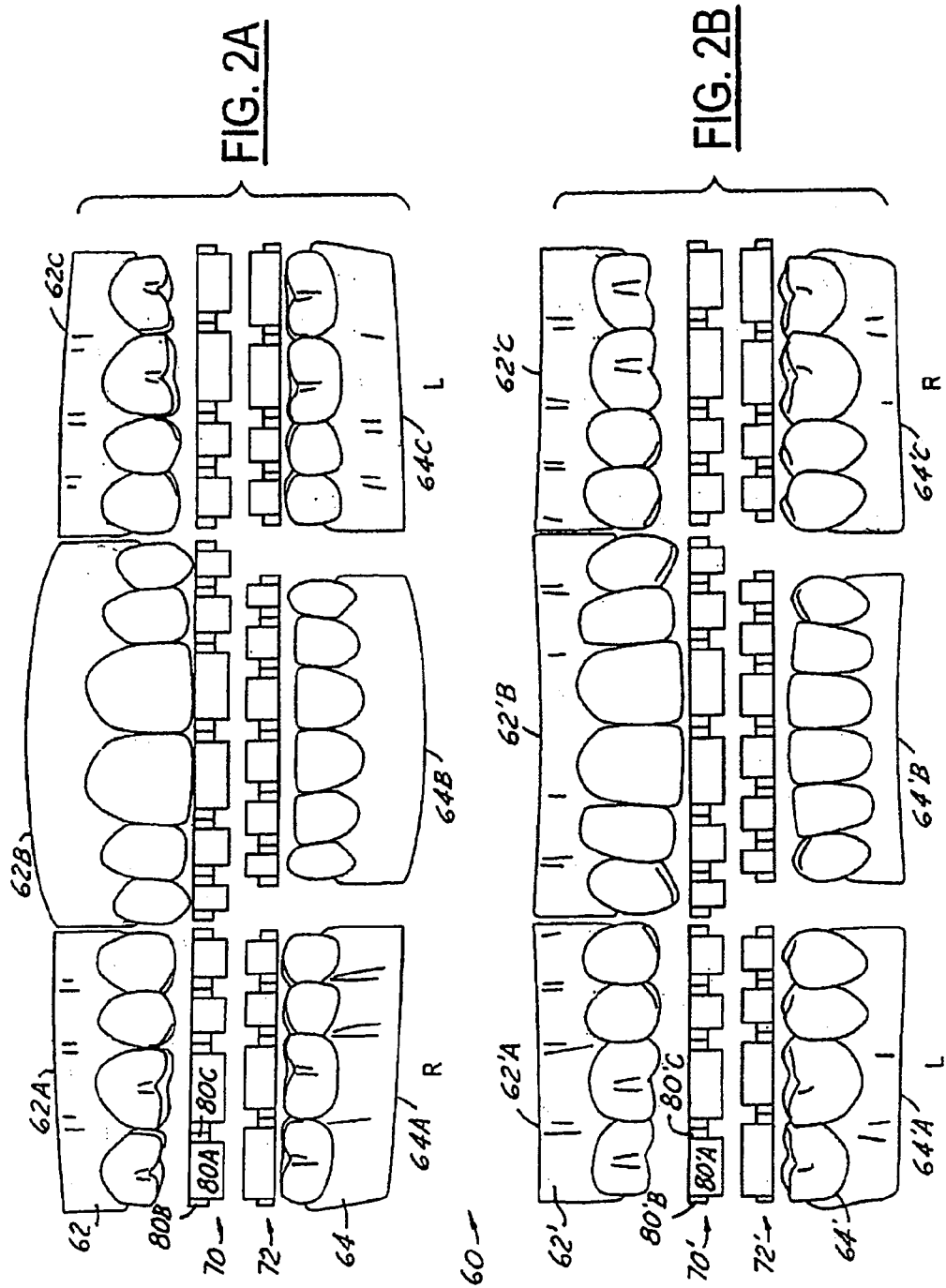

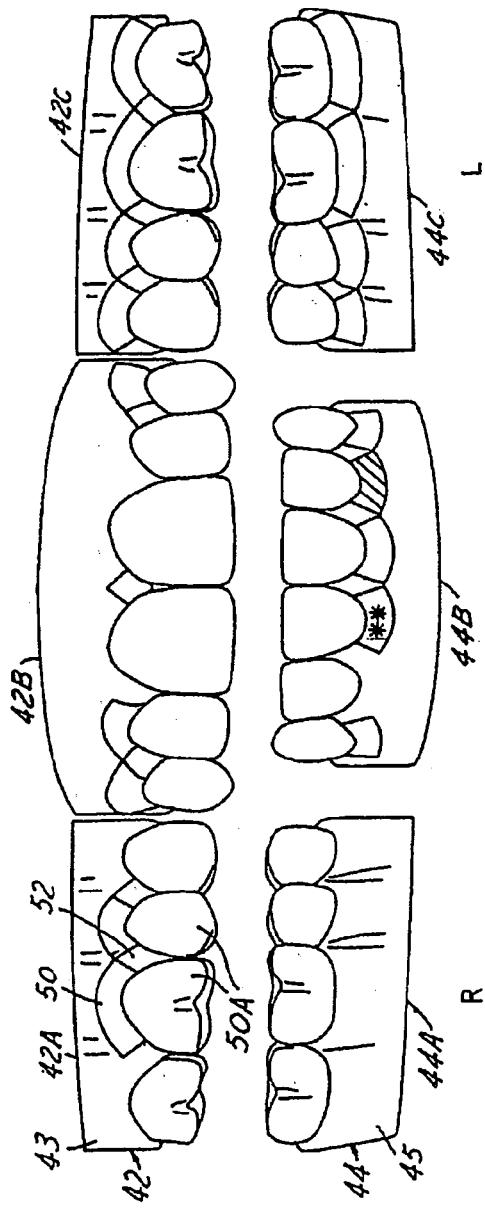
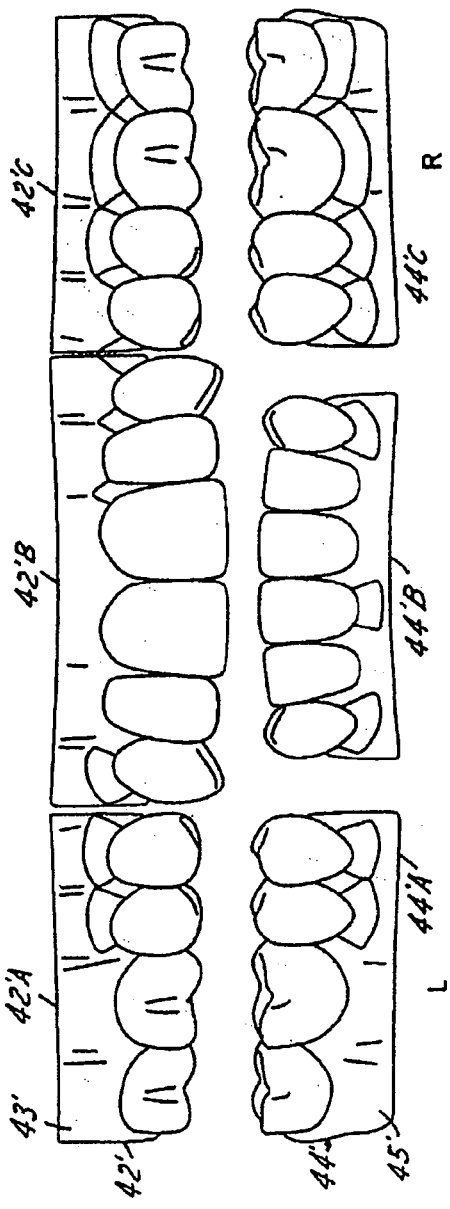
FIG. 3A
FIG. 3B

METHOD AND SYSTEM FOR PERIODONTAL CHARTING

TECHNICAL FIELD

The present invention relates to methods and systems for presenting dental data to professionals for educational purposes as well as for dental professionals to use in recommending treatment and preventative measures.

BACKGROUND OF THE INVENTION

There are many ways known today for evaluating various dental conditions, such as gingivitis and plaque. The information is taken from a patient or group of patients, evaluated and displayed in some manner for either educational, performance, or treatment use.

Some of these approaches use graphical displays that include representations of actual teeth or schematic diagrams that represent patient's teeth. Some approaches use measurement parameters as assigned scores for various dental conditions at various identified sites in the mouth.

Traditional approaches such as means-based analysis, however, are often difficult and complex to read and understand. Some of these approaches also may not have a practical impact on treatment of the patients.

There is a need for an improved, approach for creating and presenting site wise or site by site dental clinical data in graphical presentations for use in the dental field.

SUMMARY OF THE INVENTION

It is an object of the present invention to provide a simple and improved system and method for presenting dental data. It is also an object of the present invention to provide a process for presenting dental data that demonstrates the differences between various types of treatment and can be used to assist in recommending treatment for patients with various dental conditions.

The present invention meets these objectives and provides a graphical depiction of a mouth displaying the buccal aspect of the teeth as well as the lingual aspect of the teeth. The teeth may be in single row or presented in groups, preferably with the upper teeth above and the lower teeth below on the display. The teeth may also be curvilinear with the same parameters or may be in the natural curvature of the mouth and rotated to display a certain aspect.

The present invention has particular use relative to showing improvements in gingival health and representing plaque reduction. For gingival conditions, two rows or boxes are provided between the two sets of teeth displays, the boxes representing either the marginal or papillary aspects of the gum tissue above or below each tooth. The boxes that correspond to the marginal tissue have a width equal to the distance from line angle to line angle of the tooth directly above or below. The boxes that correspond to the papillary tissue are fit to the width of the papillae above or below. A second iteration used curved bands directly on top of the marginal gum tissue and on top of the papillary gum tissue.

For plaque reduction, two rows or boxes are also provided between the upper and lower sets of teeth. The rows or boxes are positioned one above the other, with the boxes representing the mid surface of the tooth, the distal surface, and the mesial surface. The boxes that correspond to the mid-surface are fit to the width equal to the distance from line angle to line angle of the tooth directly above or below. The boxes that correspond to the distal and mesial surfaces are fit to the width of the papillae above or below the box.

Each box can represent the actual score of the dental index of interest in the first case or in the second case, the relative likelihood of improvement in gingival health based on a treatment for plaque and/or gingivitis as compared to another treatment for plaque and/or gingivitis.

Preferably, the box or bands are shaded in various colors to show various stages of disease or degrees of difference between treatments. The shades of colors correspond to actual scores of the dental index or degrees of relative likelihood of improvement. In the second case, three color schemes can be used: shades of green display results statistically significant in favor of the first treatment; shades of red show results in favor of the second treatment, and black or a neutral color represents any non-significant statistical difference between the two treatments for the likelihood of improvement for plaque and/or gingivitis. The intensity of the shades in one color corresponds to the strength of relative likelihood between the two treatments.

With the present invention, it is possible to display data in an easily understood manner that represents various dental indices and statistics to demonstrate degrees of improvement or worsening produced by treatments for various dental conditions, such as gingivitis and plaque. The invention shows every tooth in a patient's mouth, as well as the location in the mouth. The data and graphical displays also show where treatment has been effective. The treatments may include, for example, the use of mouthwash, brushing with various toothpastes, flossing, and the like. The application of local delivery antimicrobials could be explored in this model as well.

Preferably, the results presented stem from a group study where the members are exposed to, or utilize, various methods of treatment. In this manner, persons reviewing the data and graphical displays can visualize the effect of various treatments on an individual patient who has a periodontal condition and plaque accumulation, and will know which specific locations that certain treatments would be effective.

BRIEF DESCRIPTION OF THE DRAWINGS

FIGS. 1A and 1B illustrate a preferred embodiment of the present invention with respect to displaying gingival health data.

FIGS. 2A and 2B illustrate a preferred embodiment of the present invention for use with displaying plaque reduction data.

FIGS. 3A and 3B illustrate an alternative method for depicting gingival health or plaque reduction data.

DESCRIPTION OF PREFERRED EMBODIMENTS

Figure 4A:
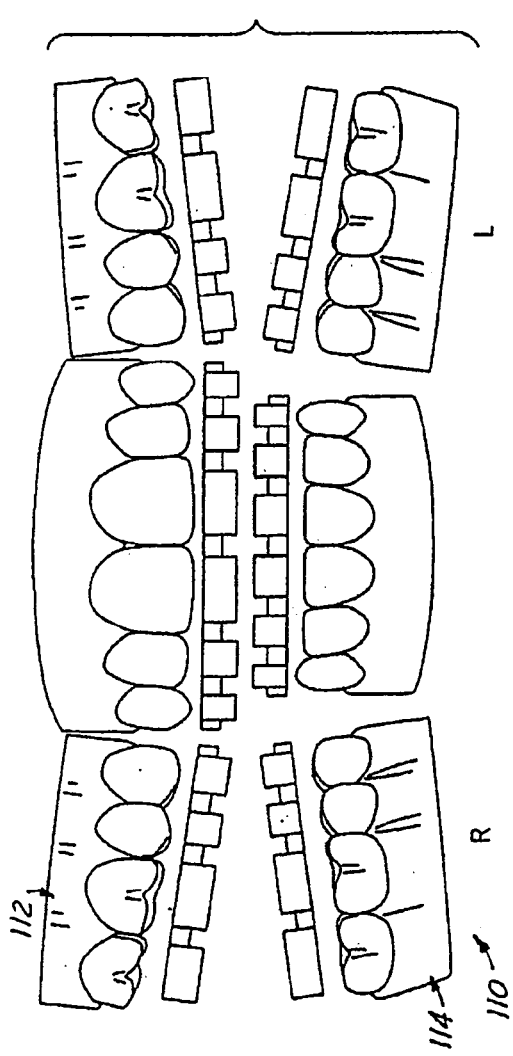
FIGS. 4A and 4B illustrate an alternate method for presentation of dental data in accordance with the present invention.

FIGS. 1A and 1B illustrate a preferred graphic depiction of gingival health data in accordance with the present invention. The graphical depiction is referred to generally by the reference numeral 10. FIG. 1A displays the buccal or outside face of the teeth, while FIG. 1B illustrates the lingual or inside face of the teeth. In FIG. 1A, the upper row or teeth are indicated by the reference numeral 12, while the lower row of teeth are indicated by the reference numeral 14. In FIG. 1B, the upper row of teeth are indicated by the reference numeral 12', while the lower row of teeth are indicated by the reference numeral 14'.

As shown in FIGS. 1A and 1B, the rows of teeth 12, 12', 14 and 14' are set out in three groups of teeth. It is possible, of course, in accordance with the present invention, to have all of the teeth be positioned in a single row or line.

Figure 4B:
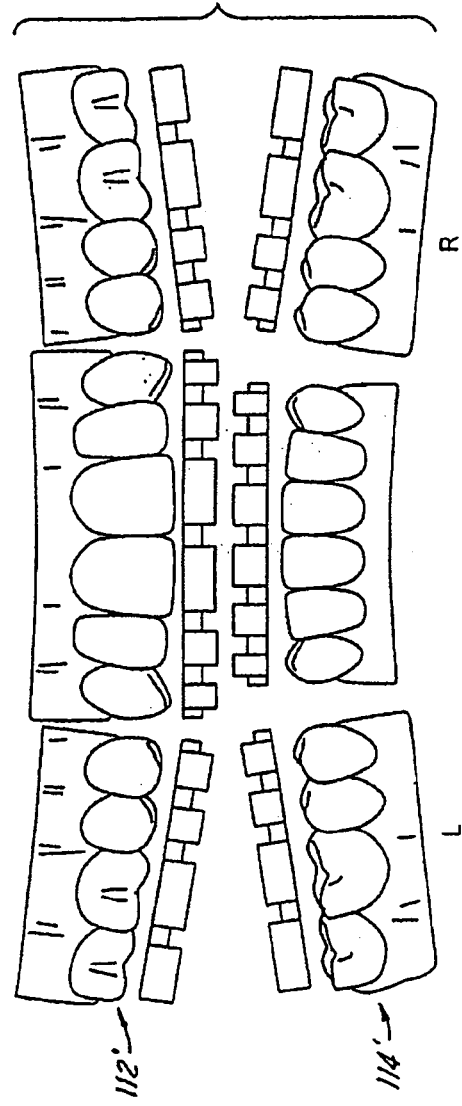

Also, as indicated in FIGS. 1A and 1B, the groups of teeth are indicated in a straight linear fashion. However, it is also possible to display the teeth in a curved or arched manner. This is shown in FIGS. 4A and 4B. In FIGS. 4A and 4B, the groups of teeth and rows of boxes are indicated by the same reference numerals as the corresponding items in FIGS. 1A and 1B, with the exception of the number "1" being added in front of the reference numerals.

Referring back to FIGS. 1A and 1B, the three groups of teeth in each of the four rows are indicated by the letters A, B, and C. For example, the three groups of teeth forming the upper buccal row of teeth 12 are indicated by the reference numerals 12A, 12B, and 12C. The letters "R" and "L" are also shown in FIGS. 1A and 1B and represent the "right" and "left" sides of a person's mouth and teeth.

Inbetween each set of the upper and lower arches or rows of teeth are positioned two rows of boxes, one above the other, which represent either the marginal or papillary aspects of the gum tissue above or below each tooth. In FIG. 1A, the row of boxes 20 corresponds to the row of teeth 12, while the row of boxes 22 corresponds to the row of teeth 14. Similarly, in FIG. 1B, the row of boxes 20' corresponds to the row of teeth 12', while the row of boxes 22' correspond to the row of teeth 14'. The marginal area of the gum tissue 13 is the area of the gum immediately above each of the teeth. The papillary aspect of the gum tissue is the area of the gum between the teeth. In rows of boxes 20, 20', 22 and 22', the boxes which correspond to the marginal gum tissue are fit to a width equal to the distance from line angle to line angle of the tooth directly above or below, and are the length approximately the length of the tooth above or below divided by two. For example, box 30A in row of boxes 20 corresponds to tooth 30B in row of teeth 12. The term "line angle" refers to the point on the tooth while the slat starts to curve in on the surface of the tooth.

Boxes which correspond to the papillary tissue are fit to the width of the papillae above or below the teeth and are the length approximately the length of the marginal box to the right divided by two. For example, box 32A in row of boxes 20 corresponds to the papillary tissue area 32C in the gum tissue 13.

The same description applies to the remainder of the boxes in the rows of boxes 20, 22, 20' and 22', as well as the rows of teeth 12, 14, 12' and 14' and the gum tissue areas 13, 15, 13' and 15'. It is not believed necessary to describe each one in detail here. As indicated, the graphical depictions of the teeth and gums as shown in FIGS. 1A and 1B are used to represent data relative to gingival health, that is, the health of the gum tissue 13, 15, 13' and 15'. More particularly, the present invention has particular use in recording and describing the effect of various therapeutic agents for the control of gingivitis. These therapeutic agents can be, for example, mouthwashes (such as Listerine) (a product of Pfizer Consumer Healthcare), tooth brushing, or flossing.

More particularly, the present invention is used to graphically display the result of the comparison between two treatments by site on the gum tissue and teeth surfaces. In this application, the relative risk, expressed as the ratio of the rate of improvement in one therapeutic agent, say Listerine, to the rate of improvement in another treatment, say control, is used.

For each patient enrolled in the study, measurements are taken of the various marginal and papillary sites of the gum tissue to reflect the health of the gum tissues at those sites. The relative condition of the gum tissue could be recorded in various ways, such as on a scale of 1–4 as in the case of the cited index. A baseline recording of data is taken for each site in the mouth of each patient, along with various examinations periodically thereafter, and after treatment with one of the therapeutic agents, such as at three months and six months.

The improvement of the gum tissue at each site is then noted and a graphical depiction in accordance with the present invention is then prepared. The rows of boxes in-between the teeth are then marked in some manner, such as being colored with various colors or shades of colors, to represent the improvement (or lack thereof), or the relative risk of improvement caused by the various therapeutic agents and oral care treatments.

For each site in the mouth, the rate of occurrence for transitions of interest is determined for the various therapeutic agents. The rates for two therapeutic agents are then compared by means of an applicable statistical method, such as relative risk, and the graphical display is then developed. The graphical display can depict each of the therapeutic agents individually comparing within treatment differences, as well as between treatment results and analysis performed for the all of the sites in the mouth.

In one preferred embodiment of the invention, the comparison between two therapeutic agents, represented by relative risk of improvement in this application, at each of the sites is categorized by multiple shades of colors, such as green, red and black. In this application, three shades of green are used to indicate relative risks where Listerine exhibited statistically significantly higher rate of improvement than the other treatment, with lighter green meaning small treatment advantage due to Listerine, and the darkest green meaning strong advantage due to Listerine. On the contrary, three shades of a red color can be utilized to indicate relative risks where Listerine exhibited statistically significantly lower rate of improvement compared to the other treatment, with the lightest red showing slight treatment disadvantage due to Listerine (or slight treatment advantage due to the other treatment) while darkest red being severe disadvantage due to Listerine (or strong advantage due to the other treatment). In addition, another color or a neutral color (e.g., black in this application) can be used to represent non-significant statistical differences between the two treatments for the rate of improvement.

For illustrative purposes, various geometrical symbols are shown in some of the boxes in sections 12B and 14B to depict relative types and ranges of colors. For example, the cross hatching 34A and 35A illustrates that Listerine exhibited greater rate of improvement than the other treatment while the two stars 36A and 37A show that the other treatment had higher improvement rate than Listerine. The blank box 38A indicates that there is no statistical difference due to the relative treatments. Of course, it is to be understood, that any type of colors, letters, numbers, graphic, symbols, or the like can be used to depict various stages of improvement or lack of improvement in accordance with the present invention. Thus, the present invention is not limited to the use of any particular statistics, colors or the use of colors at all.

Blank boxes, such as box 38A indicate that there is no statistically significant difference due to the two treatments.

As indicated, the present invention is a prospective analysis of the exposure of gum tissue to various therapeutic agents and treatments. With the present invention, dentists and other dental professionals can quickly be apprised of the relative risk of treatment of various marginal and papillary gum tissue sites with various therapeutic agents, such as Listerine, various toothpastes, flossing, and the like.

An alternate method for graphically depicting gingival health analyses and data is shown in FIGS. 3A and 3B and represented generally by the reference numeral 40. FIG. 3A illustrates the buccal aspect of the upper teeth 42 and lower teeth 44. FIG. 3B illustrates the lingual aspect of the upper teeth 42' and the lower teeth 44'. The gum tissue itself is referred to by the reference numerals 43 and 45 in FIG. 3A and 43' and 45' in FIG. 3B.

In this alternate embodiment, markings such as marginal bands 50 and papillary "diamonds" 52 are used to present the relative risk data of the marginal and papillary aspects of the gum tissue, rather than the rows of boxes as utilized in the embodiment of FIGS. 1A and 1B. The marginal bands 50 are positioned immediately on top of the corresponding teeth, which are indicated as 50A in the example shown in FIG. 3A. The papillary diamond-shaped areas 52 are positioned between corresponding teeth and indicate the relative risk of improvement of the papillary tissue at that particular site. Again, it is believed that the reference to sites 50 and 52 are sufficient for the reader to understand that similar marginal bands and papillary diamond-shaped indicia can be presented for all of the marginal and papillary sites in the rows of teeth 42, 42', 44 and 44' and relative gum areas 43, 43', 45 and 45', in FIGS. 3A and 3B and thus it is not necessary to describe each one in detail here.

Similar to the indicia presented in the rows of boxes 20, 20', 22 and 22' which are presented in the embodiment shown in FIGS. 1A and 1B, the marginal and papillary bands in the embodiment shown in FIGS. 3A and 3B are also depicted with a color, letter, number or other graphical symbol in order to show and depict the relative risk and treatment analyses as described above.

As is obvious with a comparison of FIGS. 3A and 3B with the graphical display as indicated in FIGS. 1A and 1B, the same relative risk indicia can be presented in both graphical charts or displays, but simply in different forms.

Again, similar to the embodiment shown in FIGS. 1A and 1B, the rows of teeth and gum tissue as shown in FIGS. 3A and 3B can be presented in groups A, B, and C or a single line of teeth and gum tissue (not shown). Moreover, the line or groups of teeth and gum tissue can be presented in a straight line as shown in FIGS. 3A and 3B or presented in a more natural curved arch similar to the manner of presentation as shown in FIGS. 4A and 4B.

As indicated above, the present invention can also be used to depict and predict the relative risk or other statistics of the use of various dental therapeutic agents on the reduction of tooth plaque. The effect of therapeutic agents on the reduction of plaque can be graphically depicted as shown in FIGS. 2A and 2B. This graphical depiction is referred to generally by the reference numeral 60.

In FIG. 2A, the buccal aspect of the upper teeth is shown in row 62, while the buccal aspect of the lower teeth is shown in row 64. Similarly, the lingual aspect of the teeth are shown by rows 62' and 64' in FIG. 2B. Two rows of boxes 70 and 72 in FIG. 2A and 70' and 72' in FIG. 2B are positioned in-between the upper and lower rows of teeth. The boxes represent either the mid-surface of the tooth, the distal surface, or the mesial surface. Boxes such as 80A correspond to the mid-surface of the buccal aspect of the teeth and are fit to the width equal to the distance from line angle to line angle of the tooth directly above or below, and are of a length approximately the length of the tooth above or below divided by two. The distal and mesial surfaces of the buccal aspect of the teeth are depicted by boxes 80B and 80C respectively. These boxes are also fit to the width of the papillae above or below the box divided by two and are the length approximately the length of the marginal box to the right divided by two.

The corresponding mid-surfaces, distal surfaces, and mesial surfaces of the lingual aspect of the teeth are referred to, for example, by boxes 80'A, 80'B and 80'C respectively in FIG. 2B.

Similar to the gingivitis analysis described above with reference to FIGS. 1A, 1B, and 3A, 3B, the boxes in rows 70, 70', 72 and 72' can be shaded in different colors, provided in distinctly different colors, labeled by appropriate alphabetic, numerical, or graphic indicia, to represent the rate of improvement in plaque reduction based on various treatments with different therapeutic agents. The colors also could be used to represent the ratio of the rate of improvement in plaque reduction based on a first treatment as compared to a second treatment. A neutral or different color, number, or the like could be used in the display in the various blocks to represent non-significant statistical differences between the two treatments for the rate of improvement for plaque reduction.

With the present invention, every tooth and location in a person's mouth is illustrated, as well as every site at which therapeutic treatment can have any effect. The invention has particular use for advising dental professionals as to the effect of various treatments of plaque and gingivitis by various agents at each site in the mouth.

Figure 5A:
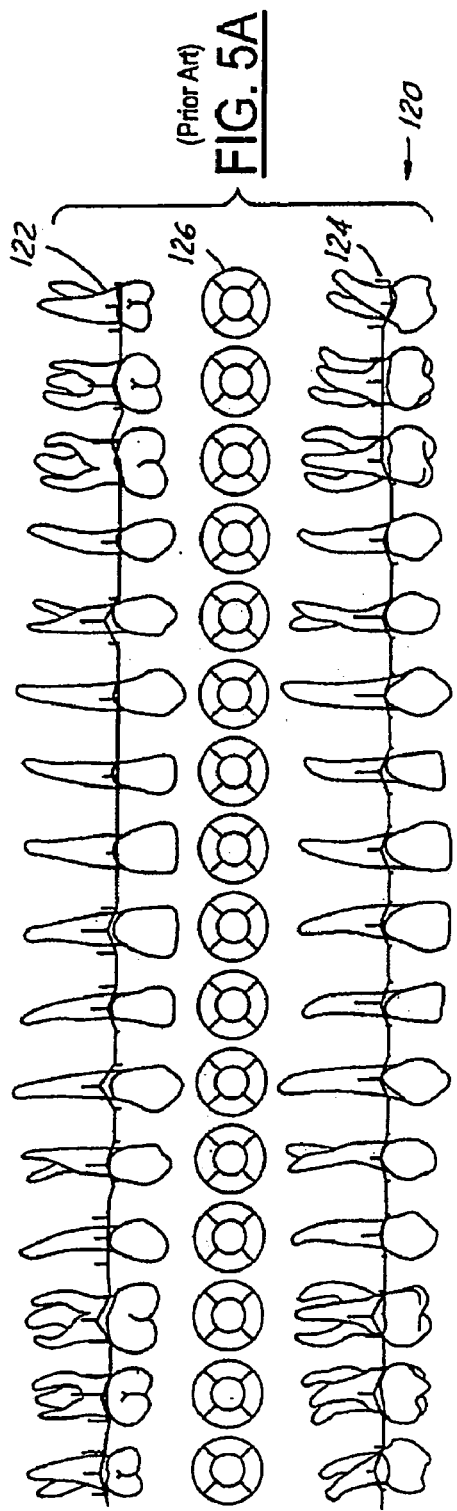
FIGS. 5A and 5B illustrate a known method for periodontal charting.
Figure 5B:
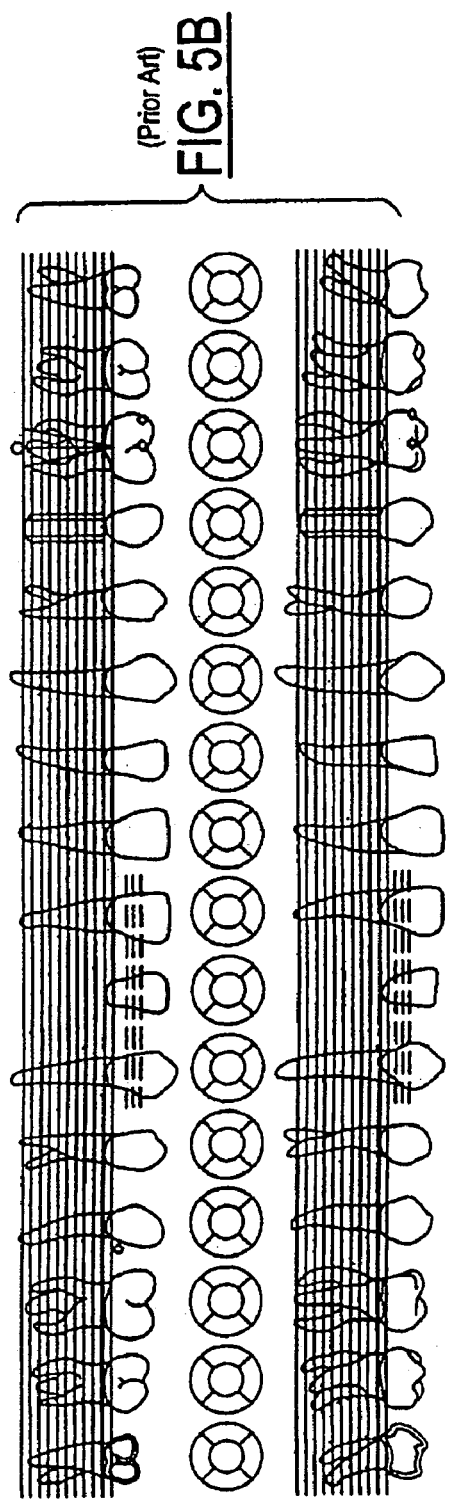

FIGS. 5A and 5B and 6A and 6B illustrate known methods for graphically displaying various dental conditions and/or plaque and gingivitis treatment. For example, FIGS. 5A and 5B illustrate the buccal and lingual aspects of the upper and lower rows of teeth, with each of the teeth being graphically displayed as actual teeth. This graphical display, which is generally referred to by reference numeral 120, illustrates the upper row of teeth 122, and the lower row of teeth 124, separated by a row of circular members 126. The circular members 126 schematically illustrate a view of each of the teeth looking at its occlusal surface and having various areas divided off so that the dentist or dental professional can indicate treatments, such as fillings, at each location of the teeth.

Figure 6A:
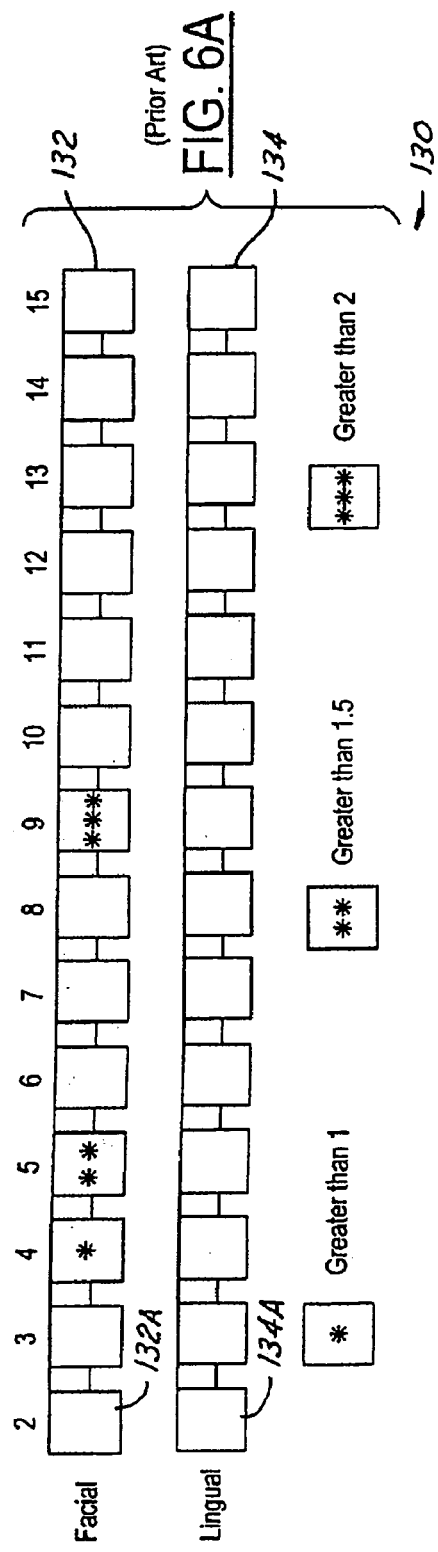
FIGS. 6A and 6B illustrate a known method of displaying gingival health analysis.
Figure 6B:
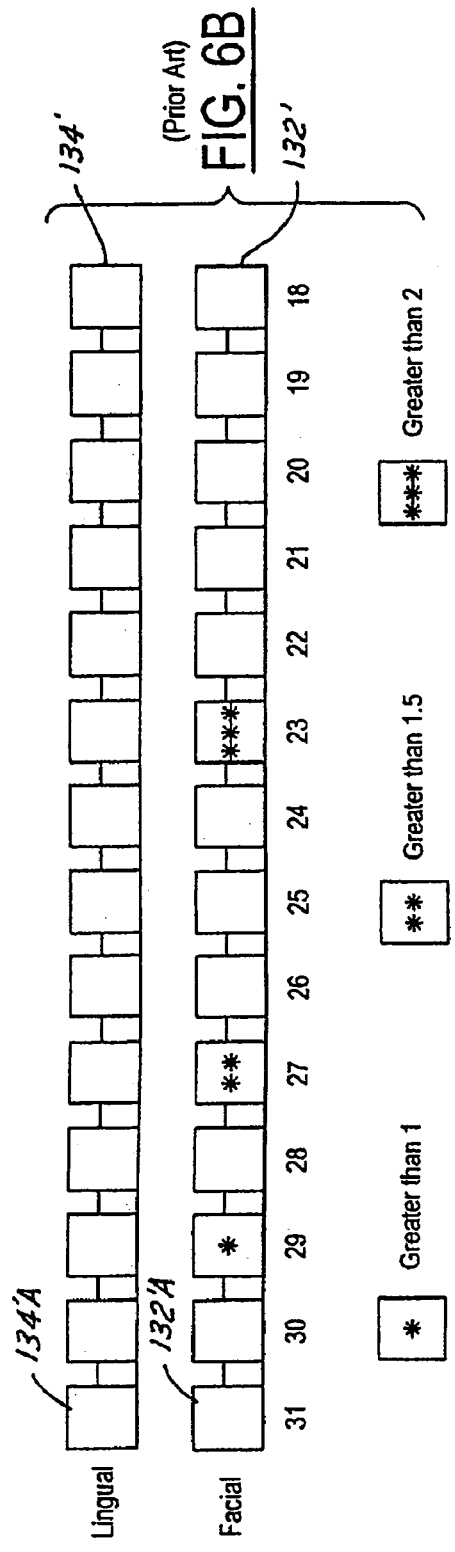

In FIGS. 6A and 6B, a method of assessing various treatment effects in gingivitis is displayed. In this system or method, which is referred to generally by the reference numeral 130, the upper teeth are depicted in FIG. 6A and the lower teeth are depicted in FIG. 6B. The front or facial sides of the upper teeth are shown in row 132, while the lingual aspect of the upper teeth are shown in row 134. Similarly, the front of the lower teeth are shown in row 132', while the lingual side of the lower teeth are shown in row 134'. As indicated, the teeth are merely referred to by numbers (2–15 and 18–31) and the boxes, such as 132A, 134A, 134'A and 132'A, are all shown of the same size and shape.

In the system 130 shown in FIGS. 6A and 6B, the graphic depiction also represents the odds ratio as compared to relative risk ratios in accordance with the present invention.

Although the description of the invention as set forth above describes the invention in terms of the relative risk of treatment comparisons, the invention is not to be limited to that subject.

While the invention has been described in connection with one or more embodiments, it is to be understood that the specific mechanisms, processes and procedures which have been described are merely illustrative of the principles of the invention, numerous modifications may be made to the methods and apparatus described without departing from the spirit and scope of the invention as defined by the appended claims.

What is claimed is:

1. A method for presenting dental data comprising the steps of:
   taking first measurements of tooth and gum tissue health relative to various tooth and gum tissue sites before treatment;
   taking second measurements of tooth and gum tissue health relative to said tooth and gum tissue sites after treatment of said sites with a dental therapeutic agent;
   determining the differences between the first and second measurements at each of said sites;
   graphically displaying said differences on a chart containing rows of teeth, gum tissue, and boxes, said boxes positioned between said teeth and said differences being displayed by predetermined markings in said boxes.

2. The method as described in claim 1 wherein said graphical display includes a row of the buccal aspect of the upper teeth, a row of the buccal aspect of the lower teeth, a row of the lingual aspect of the lower teeth.

3. The method as described in claim 2 wherein at least one row of boxes is positioned between said rows of the buccal aspect of the upper and lower teeth and at least a second row of boxes is positioned between said rows of the lingual aspect of the upper and lower teeth.

4. The method as described in claim 2 wherein two rows of boxes are positioned between said rows of the buccal aspect of the upper and lower teeth and at least two rows of boxes are positioned between said rows of the lingual aspect of the upper and lower teeth.

5. The method as described in claim 1 wherein said therapeutic agent is selected from the group comprising a mouthwash, a toothpaste, and dental floss, local delivery agent, or oral care treatment.

6. The method as described in claim 1 wherein said step of taking said first measurements comprises recording clinical observations.

7. The meted as described in claim 1 wherein said dental data that is presented comprises treatment comparison statistics including the relative risk of gum tissue health at said sites.

8. The method as described in claim 7 wherein said gum tissue health includes gingivitis.

9. The method as described in claim 1 wherein said predetermined markings are selected from the group comprising colors, shades of colors, numbers, letters and graphic indicia.

10. The meted as described in claim 1 wherein said dental data which is presented comprises the improvement or lack of improvement of gum tissue health at each of said sites.

11. A meted for presenting dental data comprising the steps of:
    taking first measurements of plaque indications at tooth sites on each of the teeth before treatment;
    taking second measurements of plaque indications at tooth sites after treatments of said sites with a dental therapeutic agent;
    determining the differences between the first and second measurements at each of said sites;
    graphically displaying said differences on a chart containing rows of teeth, gum tissue, and boxes, said boxes positioned between said teeth and said differences being displayed by predetermined markings in said boxes.

12. The method as described in claim 11 wherein said graphical display includes a row of the buccal aspect of the upper teeth, a row of the buccal aspect of the lower teeth, a row of the lingual aspect of the lower teeth.

13. The method as described in claim 11 wherein at least one row of boxes is positioned between said rows of the buccal aspect of the upper and lower teeth and at least a second row of boxes is positioned between said rows of the lingual aspect of the upper and lower teeth.

14. The method as described in claim 11 wherein two rows of boxes are positioned between said rows of the buccal aspect of the upper and lower teeth and at least two rows of boxes are positioned between said rows of the lingual aspect of the upper and lower teeth.

15. The method as described in claim 11 wherein said dental therapeutic agent is selected from the group comprising a mouthwash, a toothpaste and dental floss.

16. The method as described in claim 11 wherein said step of taking said first measurements comprises recording clinical observations.

17. The method as described in claim 1 wherein said dental data which is presented comprises treatment comparison statistics including the relative risk of plaque reduction at said sites.

18. The method as described in claim 11 wherein said predetermined markings are selected from the group comprising colors, shades of colors, numbers, letters and graphic indicia.

19. The method as described in claim 11 wherein, said dental data which is presented comprises the improvement or lack of improvement of plaque reduction at each of said sites.

20. A method for presenting dental data comprising the steps of:
    taking first measurements of gum tissue health relative to various gum tissue sites before treatment;
    taking second measurements of gum tissue health relative to said gum tissue sites after treatments of said sixes with a dental therapeutic agent;
    determining the differences between the first and second measurements at each of said sites;
    graphically displaying said differences on a chart containing rows of teeth and gum tissue, said differences being displayed in indicia positioned on the gum tissue adjacent each of the teeth.

21. The method as described in claim 20 wherein said indicia comprise arc-shaped indicia representing the marginal area of gum tissue.

22. The method as described in claim 20 wherein said indicia comprise diamond-shaped indicia representing the papillary area of gum tissue.

23. The method as described in claim 20 wherein said dental therapeutic agent is selected from the group comprising a mouthwash, a toothpaste and dental floss.

24. The method as described in claim 20 wherein said step of taking said first measurements comprises recording clinical observations.

25. The method as described in claim 20 wherein said dental data that is presented comprises treatment comparison statistics including the relative risk of gum tissue health at said sites.

26. The method as described in claim 25 wherein said gum tissue health includes gingivitis.

27. The method as described in claim 20 wherein said indicia include predetermined markings selected from the group comprising colors, shades of colors, numbers, letters and graphic designs.

28. The method as described in claim 20 wherein said dental data which is presented comprises the improvement or lack of improvement of gum tissue health at each of said sites.

29. A chart for graphically displaying oral data, said chart comprising:
- a graphical depiction of a row of teeth comprising a row of tooth representations each in the shape of and relatively positioned in said row to correspond to an actual tooth; and
- a row of boxes adjacent said row of teeth, said row of boxes comprising a set of three boxes corresponding to each tooth representation;

wherein:
each of said set of three boxes includes: a central box representing a mid surface of the actual tooth represented by the tooth representation to which said set of three boxes corresponds, a first side box representing a mesial surface of the actual tooth represented by the tooth representation to which said set corresponds, and a second side box representing a distal surface of the actual tooth represented by the tooth representation to which said set corresponds; and each of said boxes is configured to permit entry of indicia representing information relevant to the surface of the corresponding actual tooth.

30. The chart as described in claim 29, wherein said central box is wider than said first and second side boxes.

31. A chart for graphically displaying oral data, said chart comprising:
- a graphical depiction of a row of teeth and gums comprising (a) a row of tooth representations each tooth representation being in the shape of and relatively positioned in said row to correspond to an actual tooth, and (b) a gum tissue representation in the shape of actual gum tissue; and
- markings on the gum tissue representation delineating marginal gum tissue and papillae;

wherein:
said markings are configured to permit entry of indicia representing information relevant to marginal gum tissue separately from indicia representing information relevant to papillae at locations corresponding to the actual site at which the information is derived.

* * * * *